United States Patent [19]

Barone

[11] 4,179,404

[45] Dec. 18, 1979

[54] CATALYST PREPARATIVE METHOD

[75] Inventor: Bruno J. Barone, Houston, Tex.

[73] Assignee: Denka Chemical Corporation, Houston, Tex.

[21] Appl. No.: 750,920

[22] Filed: Dec. 15, 1976

[51] Int. Cl.$^2$ .............................................. B01J 27/14
[52] U.S. Cl. ...................................... 252/435; 252/437
[58] Field of Search ................................ 252/435, 437

[56] References Cited

U.S. PATENT DOCUMENTS

| B 330,354 | 1/1975 | Mount et al. ............... | 252/435 X |
|---|---|---|---|
| 3,864,280 | 2/1975 | Schneider .................. | 252/435 |
| 3,907,707 | 9/1975 | Raffelson et al. .......... | 252/437 |
| 3,975,300 | 8/1976 | Burress ...................... | 252/435 |
| 3,985,775 | 10/1976 | Harrison ..................... | 252/437 X |
| 4,016,105 | 4/1977 | Kerr ........................... | 252/435 X |

*Primary Examiner*—Delbert E. Gantz
*Assistant Examiner*—William G. Wright
*Attorney, Agent, or Firm*—Kenneth H. Johnson

[57] ABSTRACT

The preparation of phosphorus-vanadium oxidation catalyst by the reduction of the valence of vanadium to less than +5 is obtained by employing less than the stoichiometric amount of reducing agent necessary to reduce the valence of the vanadium from +5 to +4, preferably 70 to 98% of the stoichiometric amount of reducing agent can be used.

7 Claims, 2 Drawing Figures

CATALYST PREPARATIVE METHOD

BACKGROUND OF THE INVENTION

The present invention relates to an improved method of preparing catalysts for use in the oxidation of hydrocarbon to prepare dicarboxylic acids and anhydrides. More particularly, this is an improved method of preparing phosphorus-vanadium catalysts.

Basically, all of the methods disclosed in the prior art seek to obtain the vanadium in a valence state of less than 5. One method of achieving this result is to begin with vanadium in less than the +5 valence state. Another method is to start with vanadium in the +5 valence state and reduce the valency to less than +5. This invention in particular relates to the latter method.

In the reduction method, acids such as hydrochloric, hydroiodic, hydrobromic, acetic, oxalic, malic, citric, formic and mixtures thereof such as a mixture of hydrochloric and oxalic may be used. Sulphur dioxide may be used. Less desirably, sulfuric and hydrofluoric acids may be employed. Other reducing agents which may be employed are organic aldehydes such as formaldehyde and acetaldehyde; alcohols such as pentaerythritol, diacetone alcohol and diethanol amine. Additional reducing agents are such as hydroxyl amines, hydrazine, and nitric oxide.

The reducing agent can also comprise an organic acid or aldehyde reducing agent, preferably, having 1 to 18 carbon atoms, and more preferably, 1 to 8 carbon atoms; such as for example, oxalic acid, citric acid, formic acid, ascorbic acid, malic, formaldehyde, acetaldehyde or mixtures thereof and a coreducing agent comprising a secondary alcohol having 3 to 12 carbon atoms such as, isopropanol, 2-butanol, 2-pentanol, 3-pentanol, 2-octanol, 6-dodecanol, in an aqueous solution of phosphoric acid.

Generally, the reducing agents form oxysalts of vanadium. For example, if $V_2O_5$ is dissolved in hydrochloric or oxalic acid, the corresponding vanadium oxysalts are produced. These vanadium oxysalts should have as the salt forming anion an anion which is more volatile than the phosphate anion.

Trivalent phosphorus compounds may also be employed as reducing agents as particularly disclosed in U.S. Pat. No. 3,907,707.

In order to reduce the pentavalent vanadium, the prior art has quite logically employed at least a stoichiometric amount of the reducing agent and where this aspect of the catalyst preparative process has been discussed, an excess of reducing agent (theoretical amount) is preferred, e.g., U.S. Pat. No. 3,907,707 granted Sept. 23, 1975, to Raffelson et al and U.S. Ser. No. 548,163 filed Feb. 7, 1975, by Kerr now U.S. Pat. No. 4,016,105.

The present invention has as an advantage the preparation of catalysts of superior activity. It is a particular feature of the present invention that the catalysts prepared in accordance therewith are improved in conversion and/or selectivity for the partial oxidation of n-butane to produce maleic anhydride. Another feature is the attainment of a more efficient reactor utilization by higher dicarboxylic acid anhydride production per unit of catalyst per hour. A further feature of the invention is the reactor and the hot spot temperatures which are maintained at the same or reduced level as compared to less efficient catalysts prepared with excess of reducing agent.

SUMMARY OF THE INVENTION

Quite surprisingly, it has been found that superior vanadium phosphorus containing oxidation catalysts for producing dicarboxylic acid from linear $C_4$ to $C_{10}$ hydrocarbons are prepared by reducing pentavalent vanadium to a valency of less than +5 with less than a stoichiometric amount of a reducing agent.

It has been determined that the average valency of the vanadium is less than +5 and more than +4, preferably +4.1 to +4.8. The amount of reducing agent employed is preferably from about 70 to 98% of the stoichiometric amount and more preferably from about 75 to 90% of the stoichiometric amount. The stoichiometric amount is that determined theoretically and based on the amount of pentavalent vanadium present to reduce the valency of the vanadium from +5 to +4.

DRAWINGS

FIG. 1 is a plot of two sets of data from TABLE I.
FIG. 2 is a plot of two sets of data from TABLE II.

DETAILED DESCRIPTION OF THE INVENTION

Figure 1:
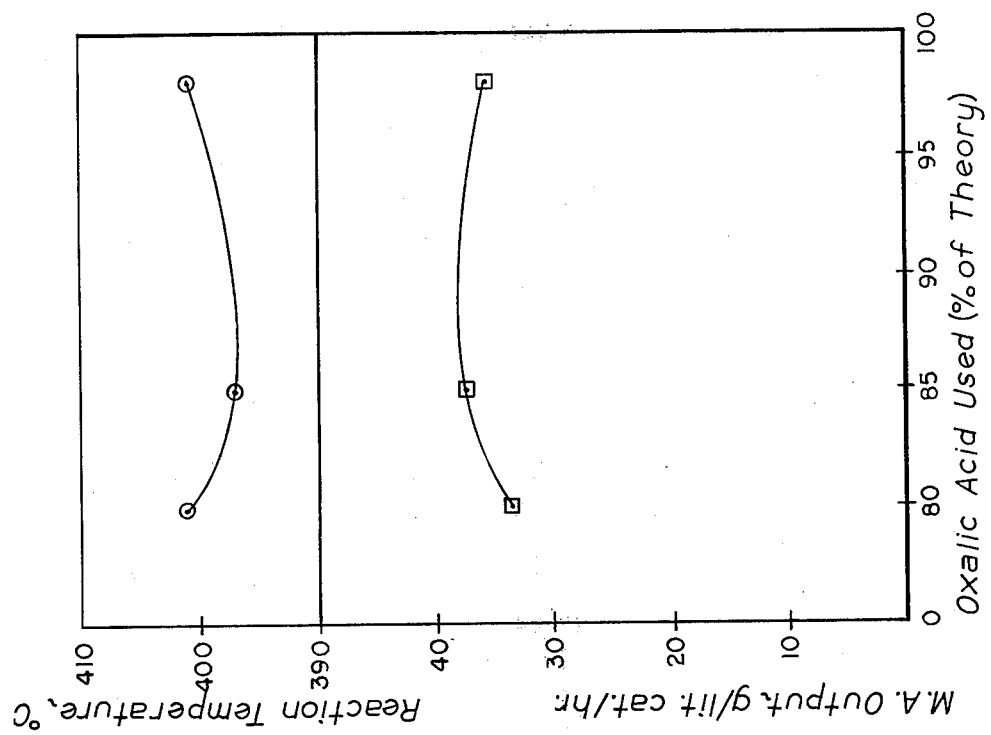
Figure 2:
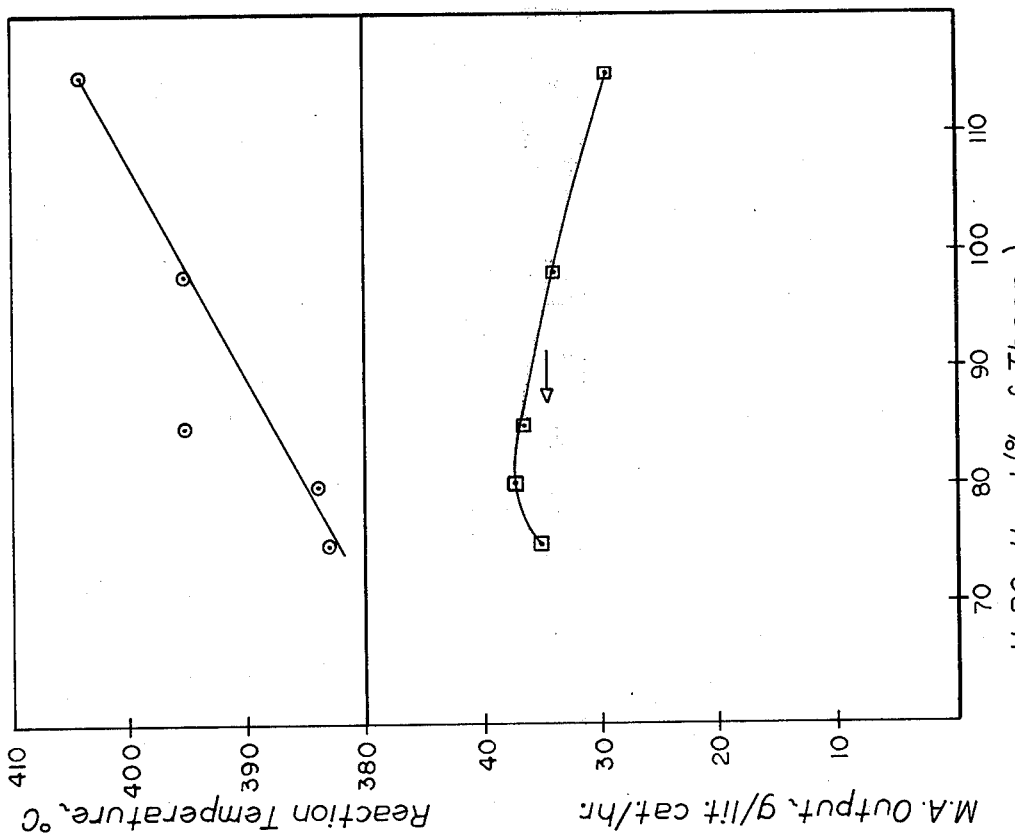

Suitable pentavalent vanadium compounds include vanadium pentoxide, ammonium metavanadate, vanadium oxytrifluoride, metavanadic acid, tetravanadic acid, pyrovanadic acid and the like. Vanadium pentoxide is preferred.

In addition to trivalent phosphorus, other phosphorus sources may be used. As an additional source of phosphorus in the catalyst precursors, pentavalent phosphorus compounds known to the art to be useful for preparing catalysts to oxidize hydrocarbons can be used. Suitable pentavalent phosphorus compounds include; phosphoric acids such as metaphosphoric acid, orthophosphoric acid, triphosphoric acid, pyrophosphoric acid and the like; phosphorus oxides such as phosphorus pentoxide and the like; phosphorus halides such as phosphorus oxyiodide, phosphorus pentachloride, phosphorus oxybromide and the like; and organophosphorus compounds such as ethyl phosphate, methyl phosphate and the like.

In addition to vanadium and phosphorus, the catalyst compositions desirably contain metallic components such as Cu, Te, Zr, Ni, Ce, W, Pd, Ag, Mn, Cr, Zn, Fe, Mo, Re, Ru, Sm, La, Hf, Ta, Th, Co, U, Sn, Nd, Y, Dy, Eu, Tb, Si, Sb, Tl, Pr or Rh. The present process has been particularly useful in preparing vanadium-phosphorus-oxygen catalysts modified with a minor amount of copper and additional metal or metalloid components.

The precise structure of the complex catalyst has not been determined, however, the complex may be represented by formula $V\ P_a Me_y O_x$, or in a more preferred composition as $V\ P_a\ Cu_b\ Me_c'\ O_x$ wherein Me is Cu, Te, Zr, Ni, Ce, W, Pd, Ag, Mn, Cr, Zn, Fe, Mo, Re, Ru, Sm, La, Hf, Ta, Th, Co, U, Sn, Nd, Y, Dy, Eu, Tb, Si, Sb, Tl, Pr, Rh, or mixtures thereof, a is 0.90 to 1.3, b is 0.005 to 0.3 and c is 0.001 (preferably 0.005) to 0.25 and y is 0.005 to 0.4 and Me' is the same as Me exclusive of Cu. These representations are not empirical formulas and have no significance other than representing the atom ratio of the active metal components of the catalysts. The x in fact has no determinate value and can vary widely depending on the combinations within the complex. That there is oxygen present is known and the $O_x$ is representative of this.

One preferable embodiment of the catalyst complex comprises vanadium-phosphorus, copper, a second metal, Mé, and an alkali or alkaline earth metal, (Alk-metal) of group IA or IIA of the Periodic Table of Elements. This complex may be represented by the configuration

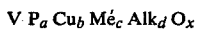

$$V\ P_a\ Cu_b\ Mé_c\ Alk_d\ O_x$$

wherein Mé, a, b, c, and x are as described above and Alk is a metal selected from the group of elements of Groups IA and IIA of the Periodic Table of Elements, and d is 0.001 to 0.1. Particular Group IA and IIA elements for the present invention are Li, Na, K, Rb, Cs, Be, Mg, Ca, Sr and Ba. Even more preferably Li, Na, Mg and Ba.

According to this method, the time at which the copper, Mé and metal compounds are incorporated into the solution is not critical so long as it is in solution before the catalyst complex is put into the form in which it is to be used. The copper, Mé and alk metal compounds may be added after the vanadium compound and the phosphorus compound have been reacted or may be added either before, at the same time or after either the vanadium or phosphorus compound has been added.

As indicated above, the present invention is applicable to the broad spectrum of solution type catalyst preparations wherein the vanadium is reduced from pentavalency to a valence of more than +4 (average valence). For example, the standard system as disclosed in Kerr's U.S. Pat. Nos. 3,156,705; 3,156,706 and 3,255,211 may be used. In the early Kerr reduction procedures, the solvent also frequently served as the reducing agent, e.g., HCl.

Reducing agents for the vanadium may be either organic or inorganic. Acids such as hydrochloric, hydroiodic, hydrobromic, acetic, oxalic, malic, citric, formic, phosphorous acids and mixtures thereof such as a mixture of hydrochloric and oxalic may be used. Sulphur dioxide may be used. Less desirably, sulfuric and hydrofluoric acids may be employed.

The catalysts are also prepared by contacting a pentavalent vanadium compound with a trivalent phosphorus compound to provide a catalyst precursor containing a substantial amount of less than +5 valence vanadium. Suitable trivalent phosphorus compounds include; phosphorous acids such as orthophosphorous acid, pyrophosphorous acid, metaphosphorous acid, hypophosphorous acid and the like; phosphorus trihalides such as phosphorus tribromide, phosphorus trichloride, phosphorus triiodide and the like; trivalent phosphorus oxides such as phosphorus trioxide and the like; organic phosphites, i.e., compounds of the type $P(OR)_3$ where R is an aryl or alkyl group such as trimethyl phosphite, triethyl phosphite, tripropyl phosphite, ethyl propyl phosphite and the like, as disclosed in U.S. Pat. No. 3,907,707 which is incorporated herein. However, phosphorous acids, such as orthophosphorous acid, are preferred.

Other reducing agents which may be employed, but which have not given as desirable catalysts are organic aldehydes such as formaldehyde and acetaldehyde; alcohols such as pentaerythritol, diacetone alcohol and diethanol amine, and additional reducing agents such as hydroxyl amines, hydrazine, and nitric oxide. The reducing agents will preferably have from one to 6 carbon atoms and be aliphatic. The reducing agent may be employed in a solvent such as oxalic acid dissolved in water or alcohol. Nitric acid and similar oxidizing acids which would oxidize the vanadium from a valence of 4 to 5 during the preparation of the catalyst should be avoided. The reducing agents may form oxysalts of vanadium. For example, if $V_2O_5$ is dissolved in hydrochloric or oxalic acid, the corresponding vanadium oxysalts are produced. These vanadium oxysalts should have as the salt forming anion an anion which is more volatile than the phosphate anion.

The time at which the other catalyst compounds, if included, are incorporated into the solution is not critical so long as it is in solution before the catalyst complex is coated onto the carrier. Heat may be applied to accelerate the formation of the complex and one method of forming the complex is by causing the ingredients to react under reflux conditions. Under reflux conditions this solution reaction generally takes about one to two hours.

Another solvent system to which the present invention is applicable is that recently disclosed in U.S. Pat. No. 3,907,707 to Raffelson et al.

To prepare the catalyst precursors by the present process, a predetermined amount of vanadium compound in which the vanadium is in the pentavalent state is contacted in an acid medium with an amount of trivalent phosphorus compound being less than the stoichiometric amount as described above. It is preferred to use phosphorous acid as the trivalent phosphorus compound which provides an acid medium to form the precursor and provides the tetravalent vanadium. The acid solution containing the trivalent phosphorus compound and the vanadium compound are heated until a blue solution is obtained, indicating that a substantial amount of the vanadium is in the tetravalent state. The amount of the time required to dissolve the phosphorus and vanadium compounds and to provide a substantial amount of the vanadium in the tetravalent state to form the catalyst precursors varies from batch to batch, depending upon the compounds used as starting materials and the temperature at which the compounds are heated. An aliquot of the solution can be analyzed to insure that the average valency of the vanadium is in the range of 4.1 to 4.8. In general, however, heating the solution to at least 100° C. for about four hours is sufficient.

The prior art catalyst may finally contain vanadium at the same average valence as that disclosed herein, i.e., 4.1 to 4.8. It is the inventor's belief that the manner of operation of the prior art and the preferences set forth therein for a stoichiometric amount or excess thereof of the reducing agent, results in some manner or degree of over reduction, which the present invention avoids, since there is insufficient reducing agent present to over reduce. The prior art generally oxidizes the catalysts after the reduction to compensate for the over reduction, but the detrimental effect of the excessive reduction is already impressed in the catalyst and is not reversed by the reoxidation. The present catalysts are calcined in air to convert the various components to oxides and little, if any, reoxidation of the reduced vanadium occurs. In any event, since there has not been an over reduction, the incidental reoxidation (as long as the catalyst has a final average valency of +4.1 to 4.8) is of no discernible importance. There may be other mechanisms or combinations thereof, which account for the improvement discovered by the present inventor and this explanation is not intended as a limitation on the invention which is described and claimed in terms of the actual improvement as physically manifested, i.e., the use of less than the stoichiometric amount of reducing agent in the process.

As an additional source of phosphorus in the catalyst precursors, pentavalent phosphorus compounds known to the art to be useful for preparing catalysts to oxidize hydrocarbons can be used. Suitable pentavalent phosphorus compounds include: phosphoric acids such as metaphosphoric acid, orthophosphoric acid, triphosphoric acid, pyrophosphoric acid and the like; phosphorus oxides such as phosphorus pentoxide and the like; phosphorus halides such as phosphorus oxyiodide, phosphorus pentachloride, phosphorus oxybromide and the like; and organophosphorus compounds such as ethyl phosphate, methyl phosphate and the like. However, phosphoric acids, such as orthophosphoric acid, and phosphorus pentoxide are preferred.

The present invention, as noted, is also applicable to the newly disclosed solvent procedure of commonly assigned application Ser. No. 548,163 filed Feb. 7, 1975, now U.S. Pat. No. 4,016,105 by Kerr which is incorporated therein. A solution of the vanadium component is prepared by adding a portion of the reducing agent, such as oxalic acid and isopropanol solution to be employed, to a solution of water and phosphoric acid and heating this mixture to a temperature generally of around 50°–80° C. A vanadium compound such as $V_2O_5$ is added incrementally to this heated mixture with stirring. The blue solution which indicates vanadium of average valency less than 5, is maintained by added increments of the remaining oxalic acid-isopropanol solution. The reducing agent comprising an organic acid or aldehyde reducing agent, preferably, having one to 18 carbon atoms, and more preferably, one to 8 carbon atoms; such as for example, oxalic acid, citric acid, formic acid, ascorbic acid, malic acid, formaldehyde, acetaldehyde or mixtures thereof and a coreducing agent comprising a secondary alcohol having 3 to 12 carbon atoms such as, isopropanol, 2-butanol, 2-pentanol, 3-pentanol, 2-octanol, 6-dodecanol, and the like.

Although the catalysts prepared by the present method may be separately formed and used as pellets, it may be more economical and practical to deposit this material on a carrier such as aluminum oxide, silica or niobium oxide. Before the carrier is combined with the catalyst the solution of catalyst is preferably concentrated to a solution which contains from about 30 to 80 percent volatiles and better results have been obtained when there is from about 50 to 70 percent volatiles by weight. The carrier may be added to the catalyst solution or the catalyst solution may be poured onto the carrier. Less desirably, the Alundum or other carrier may be present during the whole course of reactions to provide the desired vanadium-phosphorus complex. After the catalyst complex has been coated onto the carrier or pelleted, the vanadium may be converted to a more active form by heating in the presence of an oxidizing gas at a temperature in the range of 250° to 500° C. for a few minutes to several hours. Preferably air is used as the calcination atmosphere. The combination of temperature, time and atmosphere should preferably be such as to be equivalent to air for one hour at 300° C. in regard to the effect on the catalyst complex.

Suitable copper compounds are the various compounds such as the copper halides, phosphates, oxides, carbonates, sulfates, nitrates, acetates, hydrides, and so forth. Metallic copper may be used. Generally, copper compounds are used which either have the phosphate anion as the anion or which have an anion which is more volatile than the phosphate anion. Copper compounds which are soluble in hydrochloric acid are preferred. Compounds such as cuprous oxide, cupric oxide, cuprous chloride, cuprous sulfate, cuprous or cupric sulfide, cupric lactate, cupric nitrate, cupric phosphate, cuprous bromide, cuprous carbonate, cupric sulfate, cupric oxychloride, cuprous hydroxide, cuprous sulfite, cupric acetate, and the like, are useful as starting materials.

Copper is present in minor amounts but in a relatively wide range of about 0.04 to 0.20 atom of copper per atom of vanadium. The copper may be considered an "active" along with vanadium, in that it is undergoing oxidation and reduction. Phosphorus, on the other hand, is a vanadium modifier and tellurium may serve the same purpose in regard to copper. These components of the complex catalyst may serve other functions or may be characterized by others in a different manner; however, the characterization provided above may aid in understanding the mechanism of this catalyst.

The Me or Mé component is also suitably introduced by employing the various compounds thereof such as the acetates, carbonates, chlorides, bromides, oxides, hydroxides, nitrates, chromates, chromites, tellurates, sulfides, phosphates and the like. These compounds are entirely conventional and those of ordinary skill in the art know these materials and can readily determine suitable compounds to prepare the catalyst, with little, if any, experimentation. A few illustrative compounds are tellurium tetrachloride, nickel chloride, cerium (III) nitrate, tungsten dioxide, silver nitrate, manganese (II) sulfate, chromium sulfate, zinc oxalate, rhenium oxide, samarium oxalate, lanthanum hydroxide, thorium nitride, cobalt (II) orthostannate, uranyl sulfate, iron (III) oxide, tin (IV) sulfate, boron trichloride, and similar compounds.

The alk-metal may suitably be introduced as compounds such as alkali and alkaline earth metal salts with examples being lithium acetate, lithium bromide, lithium carbonate, lithium chloride, lithium hydroxide, lithium iodide, lithium oxide, lithium sulfate, lithium orthophosphate, lithium meta-vanadate, potassium sulfate, potassium chloride, potassium hydroxide, sodium chloride, sodium hydroxide, rubidium nitrate, cesium chloride, beryllium nitrate, beryllium sulfate, magnesium sulfate, magnesium bromide, magnesium carbonate, calcium carbonate, calcium chromite, strontium chloride, strontium chromate, barium acetate, barium chloride, barium tellurate, radium carbonate and the like. Mixtures of two or more alk metal compounds may be used, such as a mixture of lithium hydroxide and sodium chloride or a mixture of lithium chloride and potassium chloride.

Preferred alk-metal elements are lithium, sodium and potassium, and mixtures thereof, with lithium being particularly preferred. When the above described solution method of catalyst preparation is employed, the alkali metal compound will suitably be an alkali metal compound which either has a phosphate anion as the anion, that is a compound such as lithium phosphate, or a compound which has an anion which is more volatile than the phosphate anion.

The function of the Group IA element is not completely understood but superior results are obtained when the catalyst contains these elements. Longer useful catalyst life has been observed when the IA element is present, probably due, at least in part, to the partially stabilizing effect of the alkali on phosphorus, copper and tellurium.

The atomic ratio of the total atoms of Group IA elements to vanadium should be about 0.003 to 0.08 atom of alkali per atom of vanadium. The preferred amount of alkali is about 0.01 to 0.04 atom per atom of vanadium.

A catalyst support, if used, provides not only the required surface for the catalyst, but gives physical strength and stability to the catalyst material. The carrier or support normally has a low surface area, as usually measured, from about 0.001 to about 5 square meters per gram. A desirable form of carrier is one which has a dense non-absorbing center and a rough enough surface to aid in retaining the catalyst adhered thereto during handling and under reaction conditions. The carrier may vary in size but generally is from about $2\frac{1}{2}$ mesh to about 10 mesh in the Tyler Standard screen size. Alundum particles as large as $\frac{1}{4}$ inch are satisfactory. Carriers much smaller than 10 to 12 mesh normally cause an undesirable pressure drop in the reactor, unless the catalysts are being used in a fluid bed apparatus. Very useful carriers are Alundum and silicon carbide or Carborundum. Any of the Alundums or other inert alumina carriers of low surface may be used. Likewise, a variety of silicon carbides may be employed. Silica gel may be used.

Other materials which can serve as carriers are $Nb_2O_5$, $WO_3$, $Sb_2O_3$ and mixtures of these and other supports. The support material is not necessarily inert, that is, the particular support may cause an increase in the catalyst efficiency by its chemical or physical nature or both.

The amount of the catalyst complex on the carrier is usually in the range of about 15 to about 95 weight percent of the total weight of complex plus carrier and preferably in the range of 50 to 90 weight percent and more preferably at least about 60 weight percent on the carrier. The amount of the catalyst complex deposited on the carrier should be enough to substantially coat the surface of the carrier and this normally is obtained with the ranges set forth above. With more absorbent carriers, larger amounts of material will be required to obtain essentially complete coverage of the carrier. In a fixed bed process the final particle size of the catalyst particles which are coated on a carrier will also preferably be about $2\frac{1}{2}$ to about 10 mesh size. The carriers may be of a variety of shapes, the preferred shape of the carriers is in the shape of cylinders or spheres. Although more economical use of the catalyst on a carrier in fixed beds is obtained, as has been mentioned, the catalyst may be employed in fluid bed systems. Of course, the particle size of the catalyst used in fluidized beds is quite small, usually varying from about 10 to about 150 microns, and in such systems the catalyst normally will not be provided with a carrier but will be formed into the desired particle size after drying from solution.

Inert diluents such as silica may be present in the catalyst, but the combined weight of the essential active ingredients of vanadium, oxygen, phosphorus, copper, Me, and alk metal should preferably consist essentially of at least about 50 weight percent of the composition which is coated on the carrier, if any, and preferably these components are at least about 75 weight percent of the composition coated on the carrier, and more preferably at least about 95 weight percent. Although this catalyst is applicable to the preparation of dicarboxylic acids from a variety of normal $C_4$ to $C_{10}$ hydrocarbons, it is of primary importance in the preparation of maleic anhydride (the dicarboxylic acid being the hydrated form thereof).

The oxidation of the n-$C_4$ hydrocarbon to maleic anhydride may be accomplished by contacting, e.g., n-butane, in low concentrations in oxygen with the described catalyst. Air is entirely satisfactory as a source of oxygen, but synthetic mixtures of oxygen and diluent gases, such as nitrogen, also may be employed. Air enriched with oxygen may be employed.

The gaseous feed stream to the oxidation reactors normally will contain air and about 0.5 to about 2.5 mol percent hydrocarbons such as n-butane. About 1.0 to about 1.5 mol percent of the n-$C_4$ hydrocarbon are satisfactory for optimum yield of product for the process of this invention. Although higher concentrations may be employed, explosive hazards may be encountered. Lower concentrations of $C_4$, less than about one percent, of course, will reduce the total yields obtained at equivalent flow rates and thus are not normally economically employed. The flow rate of the gaseous stream through the reactor may be varied within rather wide limits but a preferred range of operations is at the rate of about 50 to 300 grams of $C_4$ per liter of catalyst per hour and more preferably about 100 to about 250 grams of $C_4$ per liter of catalyst per hour. Residence times of the gas stream will normally be less than about 4 seconds, more preferably less than about one second, and down to a rate where less efficient operations are obtained. The flow rates and residence times are calculated at standard conditions of 760 mm. of mercury and at 25° C. A preferred feed for the catalyst of the present invention for conversion to maleic anhydride is a n-$C_4$ hydrocarbon comprising a predominant amount of n-butane and more preferably at least 90 mol percent n-butane.

A variety of reactors will be found to be useful and multiple tube heat exchanger type reactors are quite satisfactory. The tubes of such reactors may vary in diameter from about $\frac{1}{4}$ inch to about 3 inches, and the length may be varied from about 3 to about 10 or more feet. The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Such media may be Woods metal, molten sulfur, mercury, molten lead, and the like, but it has been found that eutectic salt baths are completely satisfactory. One such salt bath is a sodium nitrate-sodium nitrite-potassium nitrate eutectic constant temperature mixture. An additional method of temperature control is to use a metal block reactor whereby the metal surrounding the tube acts as a temperature regulating body. As will be recognized by one skilled in the art, the heat exchange medium may be kept at the proper temperature by heat exchangers and the like. The reactor or reaction tubes may be iron, stainless steel, carbon-steel, nickel, glass tubes such as Vycor and the like. Both carbon-steel and nickel tubes have excellent long life under the conditions of the reactions described herein. Normally, the reactors contain a preheat zone of an inert material such as $\frac{1}{4}$ inch Alundum pellets, inert ceramic balls, nickel balls or chips and the like, present at about one-half to one-tenth the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the $C_4$ concentration. Under usual operating conditions, in compliance with the preferred procedure of this invention, the temperature in the center of the reactor, measured by thermocouple, is about 375° C. to about 550° C. The range of temperature preferably employed in the reactor, measured as above, should be from about 400° C. to about 515° C. and the best results are ordinarily obtained at temperatures from about 420° C. to about 470° C. Described another way, in terms of salt bath reactors with carbon steel reactor tubes about 1.0 inch in diameter, the salt bath temperature will usually be controlled between about 350° C. to about 550° C. Under normal conditions, the temperature in the reactor ordinarily should not be allowed to go above about 470° C. for extended lengths of time because of decreased yields and possible deactivation of the novel catalyst of this invention.

The reaction may be conducted at atmospheric, super-atmospheric or below atmospheric pressure. The exit pressure will be at least slightly higher than the ambient pressure to insure a positive flow from the reaction. The pressure of the inert gases must be sufficiently high to overcome the pressure drop through the reactor.

The maleic anhydride may be recovered by a number of ways well known to those skilled in the art. For example, the recovery may be by direct condensation or by adsorption in suitable media, with subsequent separation and purification of the maleic anhydride.

In the following examples, two types of reactors were employed. The results of the tests in the two reactors are qualitatively comparable, i.e., an increase in maleic anhydride yield in the smaller equipment will be reflected in the larger equipment, although the absolute numbers are different.

The reactor used in the following examples comprised a 4-tube cylindrical brass block (8" O.D.×18") reactor made of alloy 360. The block was heated by two 2500 watt (220 volt) cartridge heaters controlled by means of a 25 amp. thermoelectric proportional controller with automatic reset. Prior to its insulation, the block was tightly wound with a coil of ⅜" copper tubing. This external coil was connected to a manifold containing water and air inlets for cooling of the reactor block. The reactors were made of a 304 stainless steel tube, 1.315" O.D. and 1.08" I.D., 23½" long, containing a centered ⅛" O.D. stainless steel thermocouple well. The lower end of the reactor was packed with a 1" bed of 3 mm pyrex beads. The next 12" of the reactor were packed with catalyst (3/16×3/16 pellets - 160 ml) followed by about a 10" bed of 3 mm pyrex beads. The gas streams are separately metered into a common line entering the top of the reactor. The reaction vapors are passed through two 2000 ml. gas scrubbing bottles containing 800 ml. of water. The vapors from the scrubbers then go through a wet test meter and are vented. The inlet gases are sampled before entering the reactor and after the water scrubbers. The feed is normally 0.5 to 1.8 mol % $C_4$, e.g., n-butane, in air, adjusted to maintain a desired temperature. In addition, operating temperature can be further controlled by dilution of the air with an inert gas.

The inlet gases and water scrubbed outlet gases were analyzed by gas chromatography using the peak area method. Butane, carbon dioxide and any olefins or diolefins present in the gas streams were determined using a ¼" column with a 5' foresection, containing 13 wt. % vacuum pump oil on 35/80 mesh chromosorb, followed by a 40' section containing 26 wt. % of a 70–30 volume ratio of propylene carbonate to 2,4-dimethylsulfolane on 35/80 mesh chromosorb. The analysis was conducted at room temperature with hydrogen as the carrier gas (100 ml/minute). Carbon monoxide was analyzed on a ¼" column with a 3' foresection of activated carbon followed by a 6' section of 40/50 mesh 5A molecular sieves. This analysis was run at 35° C. with helium as the carrier gas (20 psi).

The water scrub solutions were combined and diluted to 3000 ml. in a volumetric flask. An aliquot of this solution was titrated with 0.1 N sodium hydroxide solution to determine maleic acid (first end point) and weak acids in solution and titrated to determine the carbonyls, using hydroxylamine hydrochloride.

EXAMPLES

CATALYSTS PREPARATION

Example 1

Into a 3 liter glass pot is charged 800 ml of deionized water, 50 ml of isopropanol, 70 ml HCl, 227.16 g of 85% $H_3PO_4$, and 106.2 g of oxalic acid 2 $H_2O$ (98% of theory). The vessel is heated and 154.53 g of $V_2O_5$ are incrementally added to maintain a blue vanadyl phosphate solution. When the reduction is complete, the solution is transferred to a concentrator and reduced to one-third its volume. The activator elements are then added: $NiCl_2.2H_2O$ (7.04 g), $CuCl_2.2H_2O$ (26.08 g), $CoCl_2.6H_2O$ (9.07 g), $CrO_3$ (0.31 g), $MoO_3$ (3.07 g), $BaCl_2.2H_2O$ (4.91 g), $NdCl_3.6H_2O$ (6.71 g), $CeCl_3.6H_2O$ (13.67 g), $Y_2O_3$ (0.82 g), and $Sm_2O_3$ (0.47 g). The solution is heated to a paste-like consistency and dried overnight in an oven at 135° C. It was broken up and calcined in air at 300° C. for one hour and tableted.

Example 2

Same composition as Example 1 but made with 91.09 g of oxalic acid.$2H_2O$ (85% of theory).

Example 3

Same composition as Example 1 but made with 85.73 g of oxalic acid.$2H_2O$ (80% of theory).

Example 4

The equipment was the same as described in Example 1 and components the same. The oxalic acid reducing agent was replaced with a 30% solution of phosphorous acid ($H_3PO_3$). Example 4 used 115% of theory of phosphorous acid. Catalyst preparation remained the same as Example 1.

Example 5

Same as Example 4 but 98% of theoretical $H_3PO_3$ used.

Example 6

Same as Example 4 but 85% of theoretical H₃PO₃ used.

Example 7

Same as Example 4 but 80% of theoretical H₃PO₃ used.

Example 8

Same as Example 4 but 75% of theoretical H₃PO₃ used.

The use of a small amount of HCl in all 8 examples was to enchance solubility of reduced vanadium. The absence of free chlorine, by chemical analysis, showed the small amount of HCl used did not assist in the reduction of the vanadium pentoxide. The same procedure for evaluation was followed for each catalyst and the results are presented in the two following tables and depicted quite graphically in the drawings.

In FIG. I the data from TABLE I showing the improvement in both maleic anhydride output and reaction temperature as a function of the percent of reducing agent (Examples 1–3). FIG. II shows substantially the same improvement (Examples 4–8), (the temperature continues to drop as the percent of reducing agent is lowered, which is desirable, except that the maleic anhydride output is also dropping off).

amount of reducing agent necessary to reduce the valency of the vanadium from +5 to +4.

2. The process according to claim 1 wherein the trivalent phosphorus compound is selected from the group consisting of orthophosphorous acid, pyrophosphorous acid, metaphosphorous acid, hypophosphorous acid, phosphorus tribromide, phosphorus trichloride, phosphorus triiodide, phosphorus trioxide, trimethyl phosphite, triethyl phosphite, tripropyl phosphite, and ethyl propyl phosphite.

3. The process according to claim 2 wherein the reducing agent is phosphorous acid.

4. In the process for the preparation of vanadium - phosphorus containing catalysts comprising the reduction of pentavalent vanadium to a valence of less than +5 wherein the reducing agent is a mixture of an organic acid or aldehyde having 1 to 18 carbon atoms and a secondary alchol having 3 to 12 carbon atoms wherein the improvement comprises employing from about 75 to 90% of the stoichiometric amount of reducing agent necessary to reduce the valency of the vanadium from +5 to +4.

5. The process according to claim 4 wherein acid or aldehyde is selected from the group consisting of oxalic acid, citric acid, formic acid, ascorbic acid, malic acid, formaldehyde and acetaldehyde and said alcohol is selected from the group consisting of isopropanol, 2-butanol, 2-pentanol, 3-pentanol, 2-octanol and 6-dodecanol.

6. The process according to claim 4 wherein the reducing agent contains oxalic acid.

7. The process according to claim 4 wherein the reducing agent is about 85% of the stoichiometric amount.

TABLE 1

OXALIC ACID REDUCTION STUDY

| Ex. | Temp., °C. Block | Temp., °C. Hot Spot | Mole % C₄-Feed | GHSV V/V/H | Hrs. On Stream | Mole % M.A. C | Mole % M.A. S | Y[b] | M.A. Output[a] g/lit./cat./hr. | Remarks |
|---|---|---|---|---|---|---|---|---|---|---|
| 1 | 401 | 455 | 0.866 | 2440 | 474 | 69.2 | 56.1 | 39 | 36. | 98% of theory |
| 2 | 397 | 450 | 0.901 | 2441 | 501 | 69 | 56.4 | 39 | 37.5 | 85% of theory |
| 3 | 401 | 455 | 0.802 | 2439 | 474 | 69 | 56 | 39 | 33.1 | 80% of theory |

[a] Output from standard benzene run is 34.2 g (using benzene as the feed over a different catalyst. At approximately 75% of benzene output n-butane is equal to benzene process economically.)
[b] C = conversion, S = selectivity, Y = yield

TABLE 11

PHOSPHOROUS ACID REDUCTION

| Ex. | Temp., °C. Block | Temp., °C. Hot Spot | Mole % C₄ Feed | GHSV V/V/H | Hrs. On Stream | Mole % M.A. C | Mole % M.A. S | Y[b] | M.A. Output[a] g/lit/cat./hr. | Remarks |
|---|---|---|---|---|---|---|---|---|---|---|
| 4 | 404 | 453 | 0.881 | 2441 | 522 | 56. | 56. | 32 | 29.7 | 115% of thoery + 70 ml HCL |
| 5 | 395 | 455 | 0.778 | 2438 | 429 | 70.3 | 57.7 | 40.6 | 33.9 | 98% of theory + 70 ml HCL |
| 6 | 395 | 450 | 0.802 | 2439 | 429 | 74.2 | 56.5 | 41.9 | 36.3 | 85% of theory + 70 ml HCL |
| 7 | 384 | 451 | 0.859 | 2440 | 451 | 70.4 | 57.2 | 40.3 | 37.0 | 80% of theory + 100 ml HCl |
| 8 | 383 | 446 | 0.783 | 2438 | 667 | 69 | 60. | 41.2 | 35 | 75% of theory + 100 ml HCL |

[a] Output from standard benzene run is 34.2 g (using benzene as the feed over a different catalyst. At approximately 75% of benzene output n-butane is equal to benzene process economically.)
[b] C = conversion, S = selectivity, Y = yield

The invention claimed is:

1. In the process for the preparation of vanadium-phosphorus containing oxidation catalysts comprising the reduction of pentavalent vanadium to a valence of less than +5 with a trivalent phosphorus compound, reducing agent, wherein the improvement comprises employing from about 75 to 90% of the stoichiometric

* * * * *

UNITED STATES PATENT AND TRADEMARK OFFICE
CERTIFICATE OF CORRECTION

PATENT NO. : 4,179,404
DATED : December 18, 1979
INVENTOR(S) : Bruno J. Barone

It is certified that error appears in the above—identified patent and that said Letters Patent is hereby corrected as shown below:

Column 1, line 32 reads "malic" but should read -- malic acid --

Column 3, line 15 reads "Ba. Even" but should read -- Ba, even --

Column 3, line 18 reads "and metal" but should read -- and Alk metal --

Column 4, line 10 reads "catalyst compounds" but should read -- catalyst components --

Column 5, line 33 reads "agent comprising" but should read -- agent comprises --

Column 10, line 35 reads "acid 2 $H_2O$" but should read -- acid·2 $H_2O$ --

Column 11, line 24 reads "Fig II shows" but should read -- In Fig. II, the data from TABLE II --

Column 11, TABLE I, heading, 2nd col. reads "BlocHot Spot" but should read -- Block Hot Spot --

UNITED STATES PATENT AND TRADEMARK OFFICE
CERTIFICATE OF CORRECTION

PATENT NO. : 4,179,404
DATED : December 18, 1979
INVENTOR(S) : Bruno J. Barone

It is certified that error appears in the above—identified patent and that said Letters Patent is hereby corrected as shown below:

Column 12, line 18,
reads "secondary alchol" but should read -- secondary alcohol --

Signed and Sealed this

*Seventeenth* Day of *February 1981*

[SEAL]

Attest:

RENE D. TEGTMEYER

*Attesting Officer*     *Acting Commissioner of Patents and Trademarks*